Figure 1:
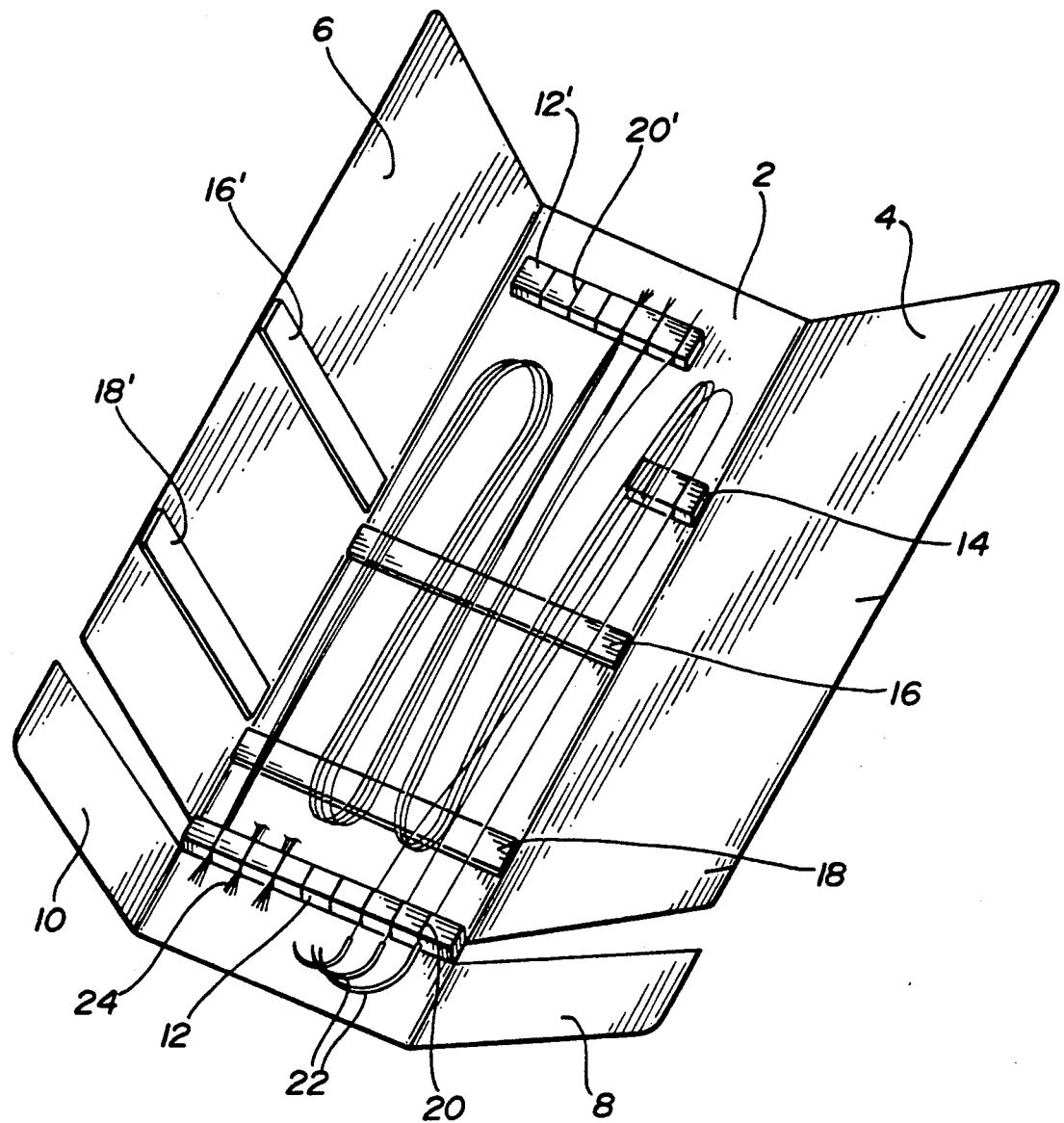

United States Patent [19]
Brunken

[11] Patent Number: 5,279,411
[45] Date of Patent: Jan. 18, 1994

[54] PACK WITH ELEMENTARY THREADS AND NEEDLE-THREAD COMBINATIONS FOR SURGICAL PURPOSES

[75] Inventor: Dieter Brunken, Huttblek, Fed. Rep. of Germany

[73] Assignee: Ethicon, Inc., Somerville, N.J.

[21] Appl. No.: 960,658

[22] Filed: Oct. 14, 1992

[30] Foreign Application Priority Data

Oct. 10, 1991 [DE] Fed. Rep. of Germany ....... 4134200

[51] Int. Cl.$^5$ ............................................. A61B 17/06
[52] U.S. Cl. .................................................. 206/63.3
[58] Field of Search ..................................... 206/63.3

[56] References Cited

U.S. PATENT DOCUMENTS

| | | | |
|---|---|---|---|
| 4,135,623 | 1/1979 | Thyen | 206/63.3 |
| 5,024,322 | 6/1991 | Holzwarth | 206/63.3 |
| 5,199,561 | 4/1993 | Roshdy et al. | 206/63.3 |

*Primary Examiner*—William I. Price
*Attorney, Agent, or Firm*—Emil Richard Skula

[57] ABSTRACT

The invention relates to a pack with elementary threads and needle-thread combinations for surgical purposes, particularly as an inner pack for double sterile packs and is characterized by (a) a base plate (2) with a front carrier ledge (12) fixed to the base plate (2) in the front region thereof between the longitudinal edges and having upwardly open guide slits (20) and a rear carrier ledge (12') fixed to the base plate (2) between the longitudinal edges at the opposite end and having upwardly open guide slits (20'), (b) one or more support ledges (16, 18) fixed between the front and rear carrier ledges (12, 12') and parallel thereto to the base plate (2), (c) several identical or different needle-thread combinations (22), as well as elementary threads (24), whose removal part is held in the guide slits (20) of the front carrier ledge (12) and whose end regions are held in the rear carrier ledge, (d) a cover plate (6), which is connected in material-integral manner with one longitudinal edge of the base plate (2) and whose surface extension covers the latter up to the front carrier ledge (12) and is wrapped over the latter and to which are fixed one or more support ledges (16', 18') in such a way that in combination with the support ledges (16, 18) on the base plate they bring about a fixing of the needle-thread combinations (22) and elementary threads (24), (e) a closure plate (4) connected in material-integral manner to the other longitudinal edge of the base plate (2) and whose surface extension is dimensioned in such a way that it can be wrapped in covering manner over the cover plate (6) covering the base plate (2) and that (f) in the front removal region the base plate (2) projects over the carrier ledge (12) and has at its two longitudinal edges a cover flap (10) and a closure flap (8) connected in material manner to said regions of the base plate (2) and which can be flapped over one another like and independently of the cover plate and the closure plate.

5 Claims, 1 Drawing Sheet

PACK WITH ELEMENTARY THREADS AND NEEDLE-THREAD COMBINATIONS FOR SURGICAL PURPOSES

The invention relates to a pack with elementary threads and needle-thread combinations for surgical purposes, particularly as an inner pack for double sterile packs.

Surgical suture material is used in the form of elementary threads having precut lengths and in the form of threads fitted with needles, i.e. needle-thread combinations. Various material types are available for threads, such as e.g. silk, polyamide, polypropylene or braided polyester in different thread thicknesses and lengths. A plurality of different straight and curved needles is used for the fitting of the threads and which differ through the needle size, needle thickness and grinding type.

The surgical suture material pack must ensure a reliable, sterile storage of the content. It must permit a rapid and reliable removal without entangling of the threads, whilst also ensuring that, following their removal, the threads do not reassume the form which they occupied in the pack (thread memory).

It has hitherto been conventional practice to offer surgical suture material in the form of one or more threads, which are identical with regards to the material type, thread thickness, thread length and needle type, or needle-thread combinations, in double sterile packs, i.e. enclosed in a primary pack and a secondary pack (overwrap). Before or during the operation, the operating room staff working under non-sterile conditions must open the overwrap of the pack, so that the operating room staff working under sterile conditions can grasp the sterile primary pack and after opening the latter can remove the elementary threads or needle-thread combinations contained therein and pass same to the surgeon. This packing procedure is a considerable burden for the operating room staff. In addition, such an individual delivery procedure is extremely time-consuming in major operations, where several different elementary threads and needle-thread combinations are required.

The problem of the invention is to propose a pack or a pack system with elementary threads and needle-thread combinations for surgical purposes, which makes it possible for the purposes of a specific operation, to make available all the different needle-thread combinations and elementary threads in the pack individually required by the surgeon for a particular operation in the form of a double sterile pack, so that following the removal of the overwrap and the primary pack with all the individual threads and needle-thread combinations required for the operation, the pack is available to the sterile-working operating room staff, which then passes the elementary threads and needle-thread combinations to the surgeon.

According to the invention this problem is solved by a pack with elementary threads and needle-thread combinations constructed according to the main claim, advantageous constructions being given in the subclaims.

The inventive pack for needle-thread combinations shown in the drawing comprises a preferably rectangular base plate 2 having a longitudinal format. In the front removal region between the longitudinal edges of the base plate 2 is fixed a carrier ledge 12, which has upwardly open guide slits 20. At the opposite end of the base plate 2 a further rear carrier ledge 12' is provided between the longitudinal edges thereof and also has upwardly open guide slits 20'. The differently dimensioned fitted needles 22 and also the elementary threads 24 are fixed in the slits in the front carrier ledge. Said threads pass in loops over the base plate 2 up to the rear carrier ledge 12' which, with its upwardly open guide slits 20', receives the end parts of the threads or the threads fitted to the needles.

The construction of the carrier ledge and in particular the front carrier ledge can be adapted to the particular requirements.

Onto the base plate 2 are stuck one or more support ledges 16 or 18 and which are fixed, e.g. by adhesion between the front and rear carrier ledges 12 or 12' and parallel thereto on the base plate 2. The elementary threads or the threads fitted to needles are placed in loop-like manner on the said base plate or on the support ledges. On the cover plate 2 connected in materially integral manner to one longitudinal edge of the base plate 2 and which in its surface extension substantially covers the base plate 2 are provided one or more support ledges, which cooperate with the corresponding support ledges on the base plate or permit a fixing of the threads. In the present embodiment the base plate 2 carries a central support ledge 16 and a further frontal support ledge 18, whilst the cover plate 6 carries a further central support ledge 16' and a corresponding support ledge 18'. These support ledges are arranged in such a way that they secure the threads and in particular the threads guided in loop-like manner in the pack. As they are preferably plastic ledges, which have a smooth surface, the threads or the threads fitted to the needles can easily be drawn out of the slits of the carrier ledge 12.

Finally, there is a closure plate 4 material-connected to the other longitudinal edge of the base plate 2 and which can be flapped over the cover plate 6 covering the base plate 2.

The front part of the base plate 2 also has a cover flap 10 material-attached to the longitudinal edge and a closure flap 8, whose surfaces are such that they can be flapped over one another.

On the base plate 2 can be provided one or more guide ledges 14 with upwardly open longitudinal slits in order to allow the threads arranged in loops on the base plate to correctly pass to the removal area. All the carrier ledges, guide ledges or support ledges are preferably made from a flexible, porous plastic having preferably a smooth surface.

The inventive pack for needle-thread combinations and elementary threads for surgical purposes with the different needle-thread combinations required for the particular operation is made available in sterilized, closed form in the separate primary pack, which is still located in the overwrap. The operating room staff working under sterile conditions, following the opening of the overwrap by the operating room staff not working under sterile conditions, merely has to grip and open the primary pack, pick out the inventive pack, open the closure flap 8 and the cover flap 10. The cover plate 6 and the closure plate 4 remain closed. The individual threads and needle-thread combinations can be gripped at the thread ends or needles available in the front removal area, so as to permit removal and handing over to the surgeon.

I claim:

1. Pack with elementary threads and needle-thread combinations for surgical purposes, particularly as an inner pack for double sterile packs, characterized by (a) a base plate with a front carrier ledge (12) fixed thereto in the front region between the longitudinal edges of the base plate and having upwardly open guide slits (20) and a rear carrier ledge (12') fixed thereto at the opposite end between the longitudinal edges of the base plate (2) and having upwardly open guide slits (20'), (b) one or more support ledges (16, 18), which are fixed between the front and rear carrier ledge (12, 12') parallel thereto on the base plate (2), (c) several needle-thread combinations (22) with the same or different material type, thread thickness, thread length and needle type, as well as elementary threads (24) of the same or different material type, thread thickness and thread length, whose removal part is kept in the guide slits (20) of the front guide ledge (12) and whose end regions are held in the rear carrier ledges, (d) a cover plate (6) connected in material-integral manner to one longitudinal edge of the base plate (2) and whose surface extension covers the base plate (2) and can be wrapped thereover up to the front carrier ledge (12) and to which are fixed one or more support ledges (16', 18') in such a way that in conjunction with the support ledges (16, 18) on the base plate they bring about a fixing of the needle-thread combinations (22) and the elementary threads (24), (e) a closure plate (4), which is connected in material-integral manner to the other longitudinal edge of the base plate (2) and whose surface extension is dimensioned in such a way that it can be wrapped over the cover plate (6) covering the base plate (2) and (f) in the front removal region the base plate (2) extends beyond the carrier ledge (12) and has on its two longitudinal edges a cover flap (10) and a closure flap (8) material-connected to said areas of the base plate (2) and which in the same way as the cover plate and the closure plate can be flapped over one another independently of the latter.

2. The pack according to claim 1, characterized in that on the base plate (2) are provided one or more guide ledges (14) with upwardly open slits.

3. The pack according to claim 1, characterized in that the carrier ledges (12, 12'), guide ledges (14) and support ledges (16, 16', 18, 18') are made from plastic and in particular flexible or foam plastic.

4. The pack according to claim 2, characterized in that the carrier ledges (12, 12'), guide ledges (14) and support ledges (16, 16', 18, 18') are made from plastic and in particular flexible or foam plastic.

5. The pack according to any one of the claims 1, 2, 3, or 4 characterized in that the needle-thread combinations (22) and the elementary threads (24) are looped several times over the support ledges (16, 18) and are secured by the corresponding support ledges (16', 18') of the cover plate (6).

* * * * *